(12) United States Patent
Munro

(10) Patent No.: US 8,222,595 B2
(45) Date of Patent: Jul. 17, 2012

(54) SPECTROMETER APPARATUS

(75) Inventor: William Angus Munro, Watford (GB)

(73) Assignee: Smiths Detection-Watford Limited, Hertfordshire (GB)

( * ) Notice: Subject to any disclaimer, the term of this patent is extended or adjusted under 35 U.S.C. 154(b) by 222 days.

(21) Appl. No.: 12/444,950

(22) PCT Filed: Oct. 22, 2007

(86) PCT No.: PCT/GB2007/004050
§ 371 (c)(1),
(2), (4) Date: Apr. 9, 2009

(87) PCT Pub. No.: WO2008/047155
PCT Pub. Date: Apr. 24, 2008

(65) Prior Publication Data
US 2010/0090100 A1    Apr. 15, 2010

(30) Foreign Application Priority Data
Oct. 19, 2006 (GB) .................... 0620748.4

(51) Int. Cl.
*H01J 49/10* (2006.01)
*H01J 49/40* (2006.01)
(52) U.S. Cl. .................. 250/287; 250/282; 250/288
(58) Field of Classification Search .......... 250/281, 250/282, 287, 288
See application file for complete search history.

(56) References Cited

U.S. PATENT DOCUMENTS

| | | |
|---|---|---|
| 3,107,966 A | 10/1963 | Bonhomme |
| 3,461,285 A | 8/1969 | Werner et al. |
| 3,470,527 A | 9/1969 | Bonhomme |
| 3,787,681 A | 1/1974 | Brunnee et al. |
| 4,378,499 A * | 3/1983 | Spangler et al. ............ 250/287 |
| 4,390,784 A * | 6/1983 | Browning et al. ............ 250/287 |
| 4,551,624 A | 11/1985 | Spangler et al. |
| 5,083,019 A | 1/1992 | Spangler |
| 5,227,628 A | 7/1993 | Turner |
| 5,304,797 A * | 4/1994 | Irie et al. ............ 250/287 |
| 5,574,277 A | 11/1996 | Taylor |
| 5,723,861 A | 3/1998 | Carnahan et al. |
| 5,854,431 A | 12/1998 | Linker et al. |
| 5,952,652 A | 9/1999 | Taylor et al. |
| 6,051,832 A | 4/2000 | Bradshaw |
| 6,073,498 A | 6/2000 | Taylor |
| 6,102,746 A | 8/2000 | Nania et al. |
| 6,225,623 B1 | 5/2001 | Turner et al. |
| 6,239,428 B1 | 5/2001 | Kunz |
| 6,442,997 B1 | 9/2002 | Megerle |
| 6,459,079 B1 | 10/2002 | Machlinski et al. |

(Continued)

FOREIGN PATENT DOCUMENTS

EP    0135747    4/1985

(Continued)

*Primary Examiner* — Jack Berman

(74) *Attorney, Agent, or Firm* — Reinhart Boerner Van Deuren s.c.

(57) ABSTRACT

An ion mobility spectrometer has several electrodes spaced along its ion source region. Voltages are applied to the electrodes to produce a voltage gradient along the length of the ion source region. By varying the voltage gradient, the residence time of ions in the ion source region can be selectively varied. Typically, the spectrometer is arranged to reduce the residence time in response to a decrease in the amplitude, of an ion peak detected at the far end of the drift region.

21 Claims, 1 Drawing Sheet

U.S. PATENT DOCUMENTS

| | | |
|---|---|---|
| 6,481,263 B1 | 11/2002 | Haley |
| 6,495,824 B1 | 12/2002 | Atkinson |
| 6,502,470 B1 | 1/2003 | Taylor et al. |
| 6,523,393 B1 | 2/2003 | Linker et al. |
| 6,825,460 B2 | 11/2004 | Breach et al. |
| 7,098,449 B1 | 8/2006 | Miller et al. |
| 7,118,712 B1 | 10/2006 | Manginell |
| 7,311,566 B2 | 12/2007 | Dent |
| 2002/0150923 A1 | 10/2002 | Malik |
| 2004/0259265 A1 | 12/2004 | Bonne |
| 2005/0017163 A1 | 1/2005 | Miller et al. |
| 2005/0095722 A1 | 5/2005 | McGill et al. |
| 2005/0161596 A1 | 7/2005 | Guevremont et al. |
| 2005/0178975 A1 | 8/2005 | Glukhoy |
| 2005/0253061 A1 | 11/2005 | Cameron et al. |
| 2006/0249673 A1 | 11/2006 | Breach et al. |

FOREIGN PATENT DOCUMENTS

| | | |
|---|---|---|
| GB | 2323165 | 9/1998 |
| WO | WO 9301485 | 1/1993 |
| WO | WO 9322033 | 11/1993 |
| WO | WO 9921212 | 4/1999 |
| WO | WO 0079261 | 12/2000 |
| WO | WO 0195999 | 12/2001 |
| WO | WO 02078047 | 10/2002 |
| WO | WO 2004012231 | 2/2004 |
| WO | WO 2006046077 | 5/2006 |
| WO | WO 2008035095 | 3/2008 |

* cited by examiner

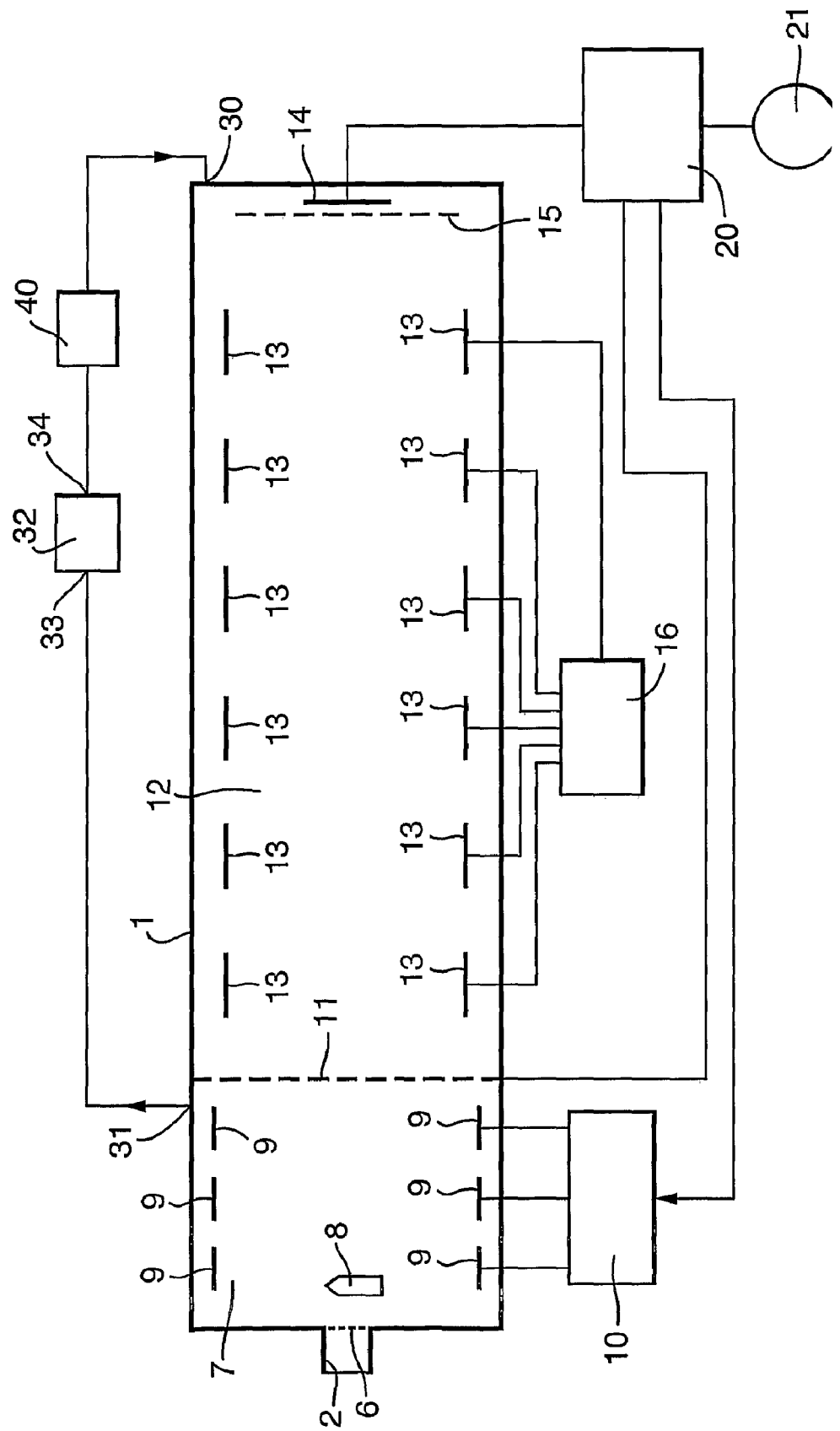

SPECTROMETER APPARATUS

BACKGROUND OF THE INVENTION

Field of the Invention

The present invention relates to spectrometer apparatus of the kind having an ion source region arranged to provide ions to an analyzer region.

Ion mobility spectrometers (IMS) apparatus and field asymmetric ion mobility spectrometers (FAIMS) or differential mobility spectrometers (DMS) apparatus are often used to detect substances such as explosives, drugs, blister and nerve agents or the like. An IMS apparatus typically includes a detector cell to which a sample of air containing a suspected substance or analyte is supplied as a gas or vapor. The cell operates at or near atmospheric pressure and contains electrodes energized to produce a voltage gradient along the cell.

Molecules in the sample of air are ionized, such as by means of a radioactive source, an ultraviolet (UV) source, or by corona discharge, and are admitted into the drift region of the cell by an electrostatic gate at one end. The ionized molecules drift to the opposite end of the cell at a speed dependent on the size of the ion. By measuring the time of flight along the cell it is possible to identify the ion. A FAIMS apparatus employs a transverse asymmetric field to filter ions.

Examples of IMS apparatus are described in U.S. Pat. No. 6,051,832, to Bradshaw et al.; U.S. Pat. No. 6,225,623, to Turner et al.; U.S. Pat. No. 5,952,652, to Taylor et al.; United Kingdom Patent No. 2,323,165, to Bradshaw; U.S. Pat. No. 4,551,624, to Spangler et al. U.S. Pat. No. 6,459,079, to Machlinski et al.; U.S. Patent Application Publication No. 2006/249673, to Breach et al.; and U.S. Pat. No. 6,495,824, to Atkinson, all of which are hereby incorporated herein by reference.

In some cases the sensitivity of such apparatus may not be sufficient for reliable detection. Also, the range of analyte concentrations over which an spectrometer apparatus can respond accurately is limited. Depletion of the charge on the reactant ion within the ion source region can cause the apparatus to saturate. This makes it difficult accurately to estimate analyte concentration.

It is accordingly desirable to provide alternative spectrometer apparatus.

SUMMARY OF THE INVENTION

According to one aspect of the present invention, there is provided a spectrometer apparatus of the above-specified kind, characterized in that the spectrometer apparatus is arranged selectively to vary the residence time of ions within the ion source region.

The apparatus may include an arrangement for establishing a voltage gradient in the ion source region, the variation in residence time being provided by varying the voltage gradient. The arrangement for establishing a voltage gradient preferably includes a plurality of electrodes spaced from one another along the ion source region. The apparatus may be arranged to vary the residence time in response to detection of ions, and may be arranged to reduce the residence time in response to an increase in amplitude of an ion peak and to increase residence time in response to a decrease in amplitude of the ion peak.

According to another aspect of the present invention, there is provided a spectrometer apparatus having an ion source region arranged to provide ions to an analyzer region, characterized in that the spectrometer apparatus includes an arrangement for applying a voltage gradient along the length of the ion source region and for varying the voltage gradient in response to detection of ions at the far end of the analyzer region.

According to a further aspect of the present invention, there is provided a method of identifying chemicals in an analyte substance including the steps of subjecting the analyte substance to ionization for a selectively controlled and variable time, subsequently measuring the mobility of the ions of the analyte substance, and deriving an indication of the nature of the ions from their measured mobility.

DESCRIPTION OF THE DRAWING

An IMS apparatus that is constructed and operated according to the teachings of the present invention will now be described by way of example, with reference to the accompanying drawing.

The FIGURE shows the spectrometer apparatus of the present invention in schematic form.

DETAILED DESCRIPTION OF THE EXEMPLARY EMBODIMENT

The system includes an IMS drift cell 1 having an inlet port 2 by which sample air to be analyzed is supplied to the apparatus. The port 2 opens into the left-hand end of the interior of the cell 1 via a selective barrier 6 such as a semi-permeable membrane, or of any other form that allows passage of the molecules of interest whilst excluding the majority of other molecules. Alternatively, the barrier 6 could be non-selective, such as a pinhole, as described in U.S. Pat. No. 6,502,470, to Taylor et al., which patent is hereby incorporated herein by reference. Instead of a barrier, the sample to be analyzed may be supplied to the cell 1 by some other interface, such as of the kind described in U.S. Pat. No. 5,574,277, to Taylor, which patent is hereby incorporated herein by reference.

The barrier 6 communicates with an ion source region 7 including an ionization source 8 such as a radiation source, UV source or a corona discharge. The ion source region 7 also includes means for producing an electric field directed generally axially of the cell. 1. The field is provided by a number of electrodes 9 spaced from one another along the length of the ion source region 7 and connected with a voltage supply 10 in a manner to be described later. To the right of the ion source region 7, a gating grid 11, such as a Bradbury Nielson gate, controls passage of ionized molecules into an analyzer region in the form of a drift region 12 formed by a series of drift electrodes 13 driven by a voltage source 16.

A collector plate 14; behind a grid 15 at the far, right-hand end of the cell 1 collects ions passed through the drift region 12 and provides an output to a processor 20, which also controls the gate 11, the voltage supply 10 and various other functions of the system. The processor 20 provides an output to a display 21, or other utilization means, indicative of the nature and concentration of the sample. Usually this is in the form of spectra of peaks of reactant ions of varying amplitudes and widths.

At its right-hand end, the cell 1 has an inlet 30, by which recirculated, cleaned, dried drift gas is supplied to the interior of the cell where it travels from right to left and flows out via an exhaust outlet 31 close to the gating grid 11 in the ion source region 7. Air is supplied to the inlet 30 by means of a pump 32 having an inlet 33 connected to the exhaust outlet 31 and an outlet 34 connected to a molecular sieve 40, which cleans and dries the air exhausted from the drift chamber 12.

The voltage supply 10 controls the voltage applied to the electrodes 9 in the ion source region 7 such as to produce a selectively variable voltage gradient or electric field along the ion source region. This controls the residence time of ions in the ion source region 7. In practice, when no analyte is detected by the collector plate 14, the voltage supply 10 controls the voltage gradient in the ion source region 7 to be a minimum value so that the ions spend a maximum time within the ion source region. In this way, there is a maximum chance of any analyte ions being ionized by the ion source 8.

When the concentration of analyte increases, this causes a decrease in amplitude of the detected reactant ion peak because ionized analyte molecules have a greater chance of losing their charge as a result of collision with non-ionized molecules. The processor 20 signals the voltage supply 10 to increase the voltage gradient or field within the ion source region 7 so that the ions more quickly away from the ion source 8 to the gating grid 11 and their residence time in the ion source region is reduced. By reducing the residence time of ions in this region 7, there is less chance for the charge on ionized analyte molecules to be depleted by contact with non-ionized molecules, so a greater number of ionized molecules enter the drift chamber 12 and drift to the collector plate 14. This increases the amplitude of ion peaks.

The processor 20 may be arranged to identify a particular ion peak of interest and to control the voltage supply 10 so that the field, and hence the residence time, is varied in response to change in amplitude of that peak. Alternatively, the apparatus may be arranged to vary the residence time in response to the amplitudes of a group of several peaks or an average over a part or all of the spectra. Information about the voltage gradient in the ion source region 7 is preferably used by the processor in determining the concentration of the analyte present, in addition to the reactant ions peak amplitudes.

There are other ways in which a voltage gradient could be established along the ion source region 7 without the need for separate electrodes 9. For example, a voltage could be applied between the ion source 8 and the gating grid 11.

The arrangement of the present invention helps to increase the sensitivity of IMS apparatus over an increased range of analyte concentrations, thereby improving its dynamic concentration range.

The invention is not confined to apparatus in which the residence time is varied by varying an electrical field since there are other ways in which the residence time can be varied selectively, such as by varying the effective length of the ion source region.

The invention is not confined to IMS apparatus but could be applied to other spectrometer apparatus such as FAIMS or DMS apparatus, such as described in International Publication No. WO 2008/035095 A1, to Atkinson et al., which is assigned of record to the assignee of the present patent application and is hereby incorporated herein by reference.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A spectrometer apparatus comprising:
    an ion source region arranged to provide ions to an analyzer region;
    a gating grid located intermediate the ion source region and the analyzer region, wherein the gating grid is arranged and configured to control the passage of ions from the ion source region to the analyzer region;
    an arrangement independent of the gating grid for establishing a voltage gradient within the ion source region;
    wherein the spectrometer apparatus is arranged and configured to selectively vary how fast or slow the ions within the ion source region move toward the gating grid by varying the voltage gradient within the ion source region.

2. A spectrometer apparatus as defined in claim 1, wherein the arrangement for establishing a voltage gradient comprises a plurality of electrodes independent from the gating grid that are spaced from one another along the ion source region.

3. A spectrometer apparatus as defined in claim 1, wherein the spectrometer apparatus is additionally comprises a plurality of drift electrodes independent from the gating grid that are arranged and configured to vary the residence time of ions within the ion source region in response to detection of ions.

4. A spectrometer apparatus as defined in claim 3, wherein the spectrometer apparatus is arranged and configured to reduce the residence time in response to an increase in amplitude of an ion peak and to increase the residence time in response to a decrease in the amplitude of the ion peak.

5. A spectrometer apparatus as defined in claim 3, wherein the spectrometer apparatus is arranged and configured to reduce the residence time in response to an increase in the concentration of the analyte and to increase the residence time in response to a decrease in the concentration of the analyte.

6. A spectrometer apparatus as defined in claim 3, wherein the spectrometer apparatus is arranged and configured to differentiate between ions of an analyte and other ions and to vary the residence time of ions within the ion source region in response to detection of analyte ions.

7. A spectrometer apparatus as defined in claim 4, wherein the spectrometer apparatus is arranged and configured to identify a particular ion peak of interest and to vary the residence time in response to changes in amplitude of that peak.

8. A spectrometer apparatus comprising:
    an ion source region arranged to provide ions to an analyzer region;
    a gating grid located intermediate the ion source region and the analyzer region, wherein the gating grid is arranged and configured to control the passage of ions from the ion source region to the analyzer region; and
    an arrangement independent of the gating grid for applying a voltage gradient along the length of the ion source region and for varying the voltage gradient in response to detection of ions at the far end of the analyzer region.

9. A method of identifying chemicals in an analyte substance comprising the steps of:

subjecting the analyte substance to ionization for a selectively controlled and variable time by varying a voltage gradient in an ion source region in which the analyte substance is ionized;

controlling the passage of ions from the ion source region to the analyzer region with a gating grid located intermediate the ion source region and the analyzer region;

wherein the voltage gradient is selectively varied independently of the gating grid to vary how fast or slow the ions within the ion source region move toward the gating grid;

subsequently measuring the mobility of the ions of the analyte substance; and deriving an indication of the nature of the ions from their measured mobility.

10. A spectrometer apparatus comprising:

a drift cell having a first end and a second end opposite said first end;

a sample inlet being located in said drift cell at said first end;

an ion source region located in said drift cell proximate said first end in which molecules of an analyte entering said drift cell through said sample inlet are ionized;

an analyzer region located in said drift cell at said second end, ions from said ion source region being provided to said analyzer region;

a gating grid located in said drift cell intermediate the ion source region and the analyzer region, wherein the gating grid is arranged and configured to control the passage of ions from the ion source region to the analyzer region; and apparatus located in said drift cell independent of the gating grid which is arranged and configured to selectively vary the residence time of ions within said ion source region by establishing a voltage gradient in said ion source region that may be selectively varied to vary how fast or slow the ions within the ion source region move toward the gating grid.

11. A spectrometer apparatus as defined in claim 10, additionally comprising:

a barrier covering said sample inlet, said barrier allowing molecules of an analyte of interest to enter said drift cell, but preventing the majority of other molecules from entering said drift cell.

12. A spectrometer apparatus as defined in claim 10, additionally comprising:

an ionization source located in an ion source region in said drift cell proximate said inlet end, said ionization source ionizing molecules of said analyte entering said drift cell through said sample inlet.

13. A spectrometer apparatus as defined in claim 10 wherein said arrangement-for establishing a voltage gradient in said ion source region comprises:

a plurality of electrodes independent from the gating grid that are spaced from one another along the length of the ion source region; and a processor operatively connected to operate said plurality of electrodes and control said voltage gradient in said ion source region.

14. A spectrometer apparatus as defined in claim 13, additionally comprising:

detection apparatus located in said analyzer region of said drift cell which detects ions provided to said analyzer region from said ion source region, wherein said processor is also operatively connected to said detection apparatus, and wherein said processor produces an output comprising spectra of peaks of reactant ions of amplitudes and widths representative of said analyte entering said drift cell and being detected by said detection apparatus.

15. A spectrometer apparatus as defined in claim 14, wherein said processor operates said plurality of electrodes in said ion source region to increase the voltage gradient to thereby reduce the residence time of ions in said ion source region in response to an increase in amplitude of spectra of peaks of reactant ions and to decrease the voltage gradient to thereby increase the residence time of ions in said ion source region in response to a decrease in the amplitude of spectra of peaks of reactant ions.

16. A spectrometer apparatus as defined in claim 10, wherein said processor is also operatively connected to operate said gating grid to control the passage of ions from said ion source region to said analyzer region.

17. A spectrometer apparatus as defined in claim 13, wherein said detection apparatus comprises:

a collector plate at said second end of said drift cell, said collector plate collecting ions passing to said second end of said drift cell and providing an output to said processor indicative of ions detected by said collector plate.

18. A spectrometer apparatus as defined in claim 10, additionally comprising:

a drift region located in the analyzer region, said drift region having a plurality of drift electrodes independent from the gating grid that are arranged and configured to generate an electrical field located therein in the drift region which draws ions away from said ion source region and toward said second end of said drift cell.

19. A spectrometer apparatus as defined in claim 18, additionally comprising:

a source of dry gas which is supplied to said drift region at a location intermediate said second end of said drift cell and is exhausted from said drift cell at a location close adjacent the downstream end of said ion source region.

20. A spectrometer apparatus as defined in claim 18, wherein said drift electrodes are arranged and configured in a plurality of pairs of spaced-apart drift electrodes which extend parallel to an axis extending from said first end of said drift cell to said second end of said drift cell.

21. A spectrometer apparatus as defined in claim 10, wherein said ion source region is arranged and configured to have a selectively variable effective length to thereby control the residence time of ions in said ion source region.

\* \* \* \* \*